(12) United States Patent
Hanoun (10) Patent No.: US 9,468,382 B2
(45) Date of Patent: Oct. 18, 2016

(54) ERGONOMIC/PHYSIOTHERAPY PROGRAMME MONITORING SYSTEM AND METHOD OF USING SAME

(75) Inventor: Reed Hanoun, Mississauga (CA)

(73) Assignee: Salient Imaging, Inc., Milford, NH (US)

( * ) Notice: Subject to any disclaimer, the term of this patent is extended or adjusted under 35 U.S.C. 154(b) by 287 days.

(21) Appl. No.: 13/255,800

(22) PCT Filed: Mar. 11, 2009

(86) PCT No.: PCT/CA2009/000303
§ 371 (c)(1),
(2), (4) Date: Oct. 14, 2011

(87) PCT Pub. No.: WO2010/111767
PCT Pub. Date: Oct. 7, 2010

(65) Prior Publication Data
US 2012/0029936 A1    Feb. 2, 2012

(51) Int. Cl.
| | |
|---|---|
| *A61B 5/0205* | (2006.01) |
| *A61B 5/103* | (2006.01) |
| *A61B 5/00* | (2006.01) |
| *G06F 19/00* | (2011.01) |
| *G06Q 50/22* | (2012.01) |

(52) U.S. Cl.
CPC .............. *A61B 5/0205* (2013.01); *A61B 5/103* (2013.01); *A61B 5/4866* (2013.01); *G06F 19/3418* (2013.01); *G06F 19/3481* (2013.01); *G06Q 50/22* (2013.01)

(58) Field of Classification Search
USPC ....................................................... 705/2, 3
See application file for complete search history.

(56) References Cited

U.S. PATENT DOCUMENTS

| | | | |
|---|---|---|---|
| 6,066,075 A | 5/2000 | Poulton | |
| 6,645,124 B1 | 11/2003 | Clem | |
| 7,537,546 B2 | 5/2009 | Watterson et al. | |
| 2002/0032583 A1* | 3/2002 | Joao | ................................. 705/2 |
| 2006/0078497 A1 | 4/2006 | Johnson | |
| 2007/0135266 A1 | 6/2007 | Dugan | |
| 2007/0156052 A1* | 7/2007 | Moore | .......................... 600/500 |
| 2007/0219059 A1 | 9/2007 | Schwartz et al. | |

FOREIGN PATENT DOCUMENTS

WO      WO 0218019 A1    3/2002

* cited by examiner

*Primary Examiner* — Sean K Hunter
(74) *Attorney, Agent, or Firm* — Hayes Soloway, P.C.

(57) ABSTRACT

A user's information uploaded onto a computer. Target data are selected and are downloaded to a wearable monitoring unit (WMU). The WMU includes a heart rate monitor, a unit accelerometer, a GPS, one or more force-micro-sensors, and an audio and/or video output. The audio/video output may provide information to the user. A display provides a continuously updated visual indication of whether the use has achieved the preselected optimum expenditures for a time segment. The WMU has an internal calendar/clock, a processor and/or memory. The processor compares measured heart rate and energy expenditure for multiple time segments against target levels stored as the user-specific wellness or rehabilitative physiotherapy program. The comparison is used to generate compliance output data.

22 Claims, 6 Drawing Sheets

ERGONOMIC/PHYSIOTHERAPY PROGRAMME MONITORING SYSTEM AND METHOD OF USING SAME

SCOPE OF THE INVENTION

The present invention relates to an ergonomic based preventative and functional rehabilitative system which allows for the daily monitoring and coaching of a user's physical and functional activities, and more preferably a system which is operable to monitor and coach one or more individuals' dynamic performance and compliance with a preselected ergonomic preventative and therapeutic or rehabilitative physiotherapy regime which, for example, is implemented to provide a rehabilitative or wellness benefit to the particular user.

BACKGROUND OF THE INVENTION

Where an individual at risk of injury, or one that has sustained an injury and is receiving disability or sickness benefits from his or her employer or an insurance company, there is an incentive to not only an employee or injured party, but also the employer or benefit provider in ensuring compliance with general wellness or rehabilitative physiotherapy regimes. In particular, the adoption of not only healthy workplace activities, but daily activities which promote cardiovascular exercise and whole body wellness, will advantageously reduce employee risk of physical injury, absenteeism and increase overall productivity. In the case of injured or ill workers, the failure to comply with a prescribed rehabilitative physiotherapy schedule lengthens the recovery times, increasing both job-loss time and benefit costs to the employer and the insurer. Furthermore, employees that fail to participate in ergonomics and functional preventative programs prescribed, increase the risk of injury.

Most strokes and serious automobile or industrial accidents which result in severe injury to an individual typically necessitate that the individual undertake a lengthy and comprehensive rehabilitative exercise regime in order to regain pre-accident wellness and/or mobility. Such regimes often require the user to undertake lengthy, and frequently physically demanding rehabilitative exercises or physiotherapy delivered at a health clinic supplemented with physical activities delivered at a health club and or at home to rebuild damaged muscle and bone tissues. There is furthermore often a direct correlation to the individual's commitment and adherence to the physiotherapy regime and the speed and effectiveness of the recovery which can hinder best clinical practices. In a worst-case scenario, the failure to adhere to a necessary physiotherapy routine may result in muscle tissues atrophying, leading to irrevocable permanent disabilities in the patient.

In addition, as a result of limited resources, scheduled physiotherapy sessions typically involve the patient spending as little as between 30 and 60 minutes with a trained physiotherapist each day. The applicant has appreciated that if a physiotherapy regime can be established over an extended time and/or over an entire waking day, week or month, health delivery programming can be administered at a lower cost at a health and fitness facility and/or supplemented with home based physical activity, and the patient's compliance thereto monitored and validated, enhanced patient recovery rates may be obtained.

SUMMARY OF THE INVENTION

The present invention provides for a system which includes a personal mobile health and fitness monitoring and coaching device or unit which stores target heart rate and/or caloric consumption data including other daily functional programming as prescribed by a healthcare provider, which correlates to a selected wellness or rehabilitative physiotherapy programme. More preferably, the monitoring and coaching unit is adapted to be worn by the user. The unit is operable to allow the user to periodically or continuously monitor and manage his or her physical state, based on physical state of activity based on knowledge and real-time analysis of heart rate, caloric expenditure, energy burn, functional and/or dynamic body movements, over a selected period, as well as compliance with a selected wellness or physiotherapeutic programme. The wearable monitoring unit is preferably operable to record and/or download data which is indicative of the user's physical activities, energy expenditure and/or physical performance over the selected period of time, as well as providing analysis and feedback based thereon. The collected data is most preferably compared or validated against preselected standards for the selected wellness or physiotherapy programme. Most preferably, the selected programme is chosen specifically having regard to a desired health or therapeutic benefit to the user.

Although not essential, in a preferred embodiment, the compared data may then be used to provide the user and/or the user's employer or other benefit provider with an indication as to whether or not compliance with the wellness or physiotherapy regime is being achieved; and whether best practices are applied.

Accordingly, one object of the invention is to provide a coaching, programming and monitoring system for ensuring compliance with a preselected wellness or physiotherapy programme which is selected to either maintain or improve the user's overall health.

Another object of the invention is to provide an outpatient physiotherapy coaching, programming and compliance monitoring system for a patient having an injury or malady in need of rehabilitative physiotherapy, and which allows for the remote monitoring an outpatient's compliance with a rehabilitative physiotherapy programme which is selected specifically to provide a therapeutic benefit to the patient, having regard to his or her injury or malady.

Another object of the invention is to provide an employer and/or patient benefit management system which is operable to maximize an individual's compliance with a selected ergonomic, wellness and/or physiotherapy programme selected to achieve a more healthy lifestyle, or to minimize ergonomic injury and the time for patient recovery, so as to reduce lost employee productivity and/or benefit costs.

In a preferred construction, a wearable monitoring unit (WMU) is provided for measuring the user's heart rate and dynamic energy and/or caloric expenditure over an extended period of time. Preferably the time period extends over the bulk of at least one waking day, and most preferably over at least one to four weeks. The wearable monitoring unit includes one or more of a heart rate monitor, a unit accelerometer, a global positioning system (GPS), and one or more force micro-sensors. Optionally the WMU may also be provided with a digital audio and/or video Mp3 player and an audio and/or video output. The audio/video output is preferably operable to provide information and/or motivational prompts to the user in the event the heart rate, energy expenditure and/or caloric expenditure falls below or exceeds preselected target expenditures over a particular time segment of the selected time period. In a preferred construction, the WMU includes a display on a front panel which is used to provide a continuously updated visual indication of whether or not the user has achieved the preselected optimum caloric burn or energy expenditure for that particular time segment. In an alternate constructions, the WMU may be provided with wireless communication capability, allowing for its interface with other exercise devices, and/or used to upload and download heart rate, dynamic energy and/or caloric expenditure data and/or programming for group activities, such as staffed or unstaffed aerobic classes and the like.

In another possible construction, the WMU is provided with an internal calendar/clock, a processor and/or memory. The processor is operable to compare wellness or measured heart rate and energy expenditures for multiple time segments against target levels stored as the user-specific wellness or rehabilitative physiotherapy programme and which are tailored to provide the maximum therapeutic benefit to the user. Preferably the comparison of the target heart rate and energy expenditures against the user's actual measured heart rate, energy and/or caloric expenditure for the actual measured time is used to generate compliance output data to either the user and/or the employer.

In one embodiment, the user's personal biometric information such as age, sex, weight, height as well as the user's lifestyle information, such as job description, smoker status and physical fitness, and any injury or malady type is input directly or uploaded via the internet onto a host computer/portal or central processing unit (CPU). Target heart rate, energy and/or caloric consumption levels related to wellness or rehabilitation goals for a particular job type and injury are then selected having regard to fitness levels for an individual of comparable age, performing a similar job function. Alternately, employers or medical professionals may select unique and/or enhanced target fitness levels having regard to a desired wellness or rehabilitative programme chosen to maximize health benefits to the employee.

Accordingly, in one aspect the present invention resides in a physiotherapy compliance monitoring system for ensuring a user's compliance with a preselected physiotherapy programme over a selected time period, the system including, a data management system including, a reference database for storing datafiles providing preferred target heart rate and joule expenditure standards for a plurality of rehabilitation programmes, said rehabilitation programmes correlated to a biometric parameter, a lifestyle profile parameter and an injury or malady type to be rehabilitated, said biometric parameters comprising at least one of said user's age and weight, a client database for storing input client data indicative of each of said user's injury or malady, said user's biometric parameters, lifestyle profile information for said user, and benefit data correlated to a user's health benefit, a processing unit operable to output as said preselected physiotherapy programme a selected one of said rehabilitation programmes correlated to said input client data, a wearable monitoring device for communicating with said data management system and being operable to measure said user's caloric and/or joule expenditure over the selected time period, the monitoring device including, an internal clock, memory for storing said preselected physiotherapy programme as downloaded user specific heart rate and joule expenditure standards over the selected time period, a heart rate monitoring sensor for monitoring and outputting heart rate data signals indicative of said user's heart rate over the selected time, at least one accelerometer for monitoring and outputting joule data signals indicative of at least one of movement by said user and physical force on at least part of said user's body over the selected time period, an internal processor for comparing said heart rate data signals and said joule data signals to said user specific heart rate and joule expenditure standards over said selected time period, and outputting a compliance output value which is dependent on the comparison, and wherein the data management system is operable to modify the user's health benefit data in response to the output value.

In another aspect, the present invention resides in an ergonomic monitoring system for monitoring and validating compliance with a preselected wellness or physiotherapy programme by a user, the system including, a data management system including, a reference database for storing a plurality of datafiles providing preferred target heart rate and caloric and/or joule expenditure standards for a plurality of wellness and rehabilitation programmes correlated to an injury, disability and a lifestyle profile, and a preselected biometric parameter, said biometric parameters comprising at least one of user age, and weight, a client database for storing client data indicative of biometric parameters of said user and at least one of a disability, injury and lifestyle profile of said user, a processing unit operable to output as said preselected wellness or physiotherapy programme a selected one of said wellness and rehabilitation programmes which correlates at least in part to at least one of said user's injury, disability and lifestyle profile, and said preselected biometric parameters, a wearable monitoring device for communicating with said data management system and being operable to measure said user's total daily caloric expenditure, the monitoring device including, an internal clock, memory for storing said selected wellness and rehabilitation physiotherapy programme as time dependent user specific heart rate and caloric and/or joule expenditure standards for a preselected time period, a heart rate monitoring sensor for monitoring and outputting heart rate data signals indicative of said user's heart rate, and an accelerometer for monitoring and outputting caloric and/or joule data signals indicative of at least one of movement by said user and physical force on at least part of said user's body, a processor for receiving said heart rate data signals and said caloric and/or joule data signals as input values and validating said input values to said user specific heart rate and caloric and/or joule expenditure standards over said preselected time period, and outputting a compliance output data indicative of any difference between said input values and said user specific heart rate and caloric and/or joule expenditure standards, a display for providing said user with a visual representation of said compliance output data.

In a further aspect, the present invention resides in a method of using a wearable monitoring device for validating a user's compliance with a physiotherapy programme selected to provide a therapeutic advantage to the user, the wearable monitoring device including a heart rate monitoring sensor for monitoring and outputting heart rate data signals indicative of said user's heart rate, and an accelerometer for monitoring and outputting caloric and/or joule data signals indicative of at least one of movement by said user and physical force on at least part of said user's body, the method comprising, providing a reference database storing a plurality of datafiles for preferred target heart rate and caloric and/or joule expenditure standards for a plurality of rehabilitation programmes, said rehabilitation programmes correlated to a preselected biometric parameters and injury type, said biometric parameters comprising at least said user's age and weight, providing a client database storing input client data indicative of a user's injury, age, weight, and benefit data, downloading to the wearable monitoring device as said physiotherapy programme a selected one of said rehabilitation programme correlated to the user's input client data, validating as input values said heart rate data signals and said caloric and/or joule data signals to said user specific heart rate and caloric and/or joule expenditure over a preselected time period, and outputting a compliance output data indicative of any difference between said input values and said user specific heart rate and caloric and/or joule expenditure, and recording a change in said benefit data in response to the compliance output data.

BRIEF DESCRIPTION OF THE DRAWINGS

Reference may now be had to the following detailed description, taken together with the accompanying drawings in which.

DETAILED DESCRIPTION OF THE PREFERRED EMBODIMENTS

Figure 1:
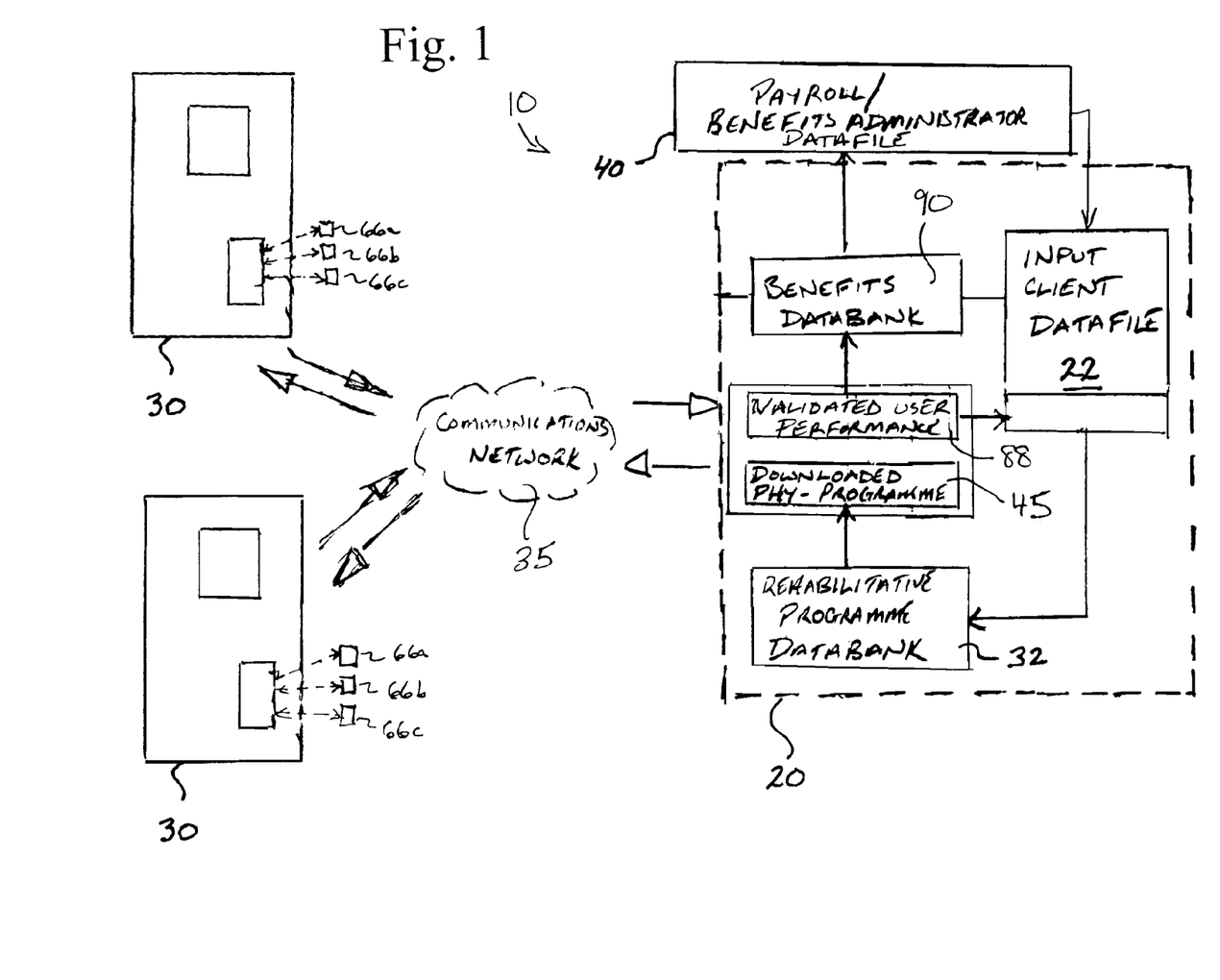
FIG. 1 shows schematically a physiotherapy compliance monitoring system in accordance with a preferred embodiment of the invention.
Figure 6:
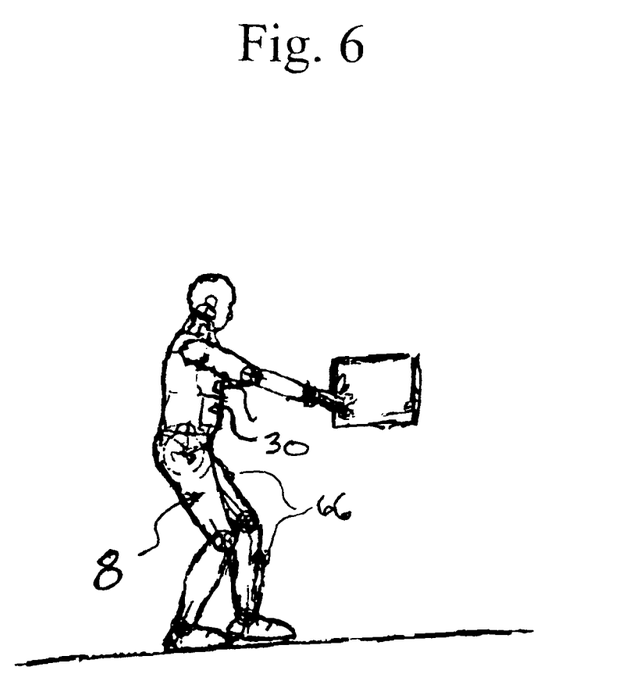
FIG. 6 illustrates schematically the wearable monitoring unit (WMU) of FIG. 2 in use in the monitoring and validation of a preselected whole-day physiotherapy programme in accordance with a preferred embodiment.

Reference is made to FIG. 1 which schematically illustrates an ergonomic monitoring system 10 which, as will be described, is most preferably used in the monitoring and validation of a user's compliance with a preselected rehabilitative physiotherapy programme. The system 10 provides an advantage over conventional fitness monitoring systems in that unlike existing systems which focus primarily on the user's health club activity over a 45 minute to 1 hour workout, the monitoring system 10 permits the monitoring and validation of compliance with a preselected physiotherapy regime over an entire waking day for periods of upto weeks or even months. The present system 10 may furthermore by used to provide not only periodic or real-time visual and aural behavioural modification guides and/or prompts to the user 8 (FIG. 6) throughout the entire day, but also allows for the adjustment of user rewards and/or benefits as added incentives to adhere to the physiotherapy programme. In a preferred method of use, the selected physiotherapy programme is chosen having regard to the individual specific need of physical rehabilitation by the user 8. By way of non-limiting examples, these could include user injury or malady, such a stroke, back injury, heart attack, or to therapeutic exercise to the user's arms or legs after an automobile or industrial accident.

The system 10 includes a central processing unit 20, and at least one, and preferably a number of portable wearable monitoring units (WMU) 30 operable to be concurrently worn by different multiple users as part of the system operation. Each WMU 30 has a size and configuration selected to be easily carried and worn by the user 8 during his or her daily waking routine, without significantly encumbering daily activities.

The central processing unit 20 is most preferably housed as part of a mainframe computer by the user's employer, insurance company, HMO, or other benefit provider or administrator, and is electronically connected to an administrator payroll or benefit datafile 40. The benefit datafile 40 may be housed on the CPU 20 itself, or alternately stored at a remote location, and electronically linked to the CPU 20 electronically via a local or global computer network connection. Housed on the central processing unit 20 is an input client datafile 22, as well as a reference datafile 32 of stored rehabilitative programmes.

Figure 3:
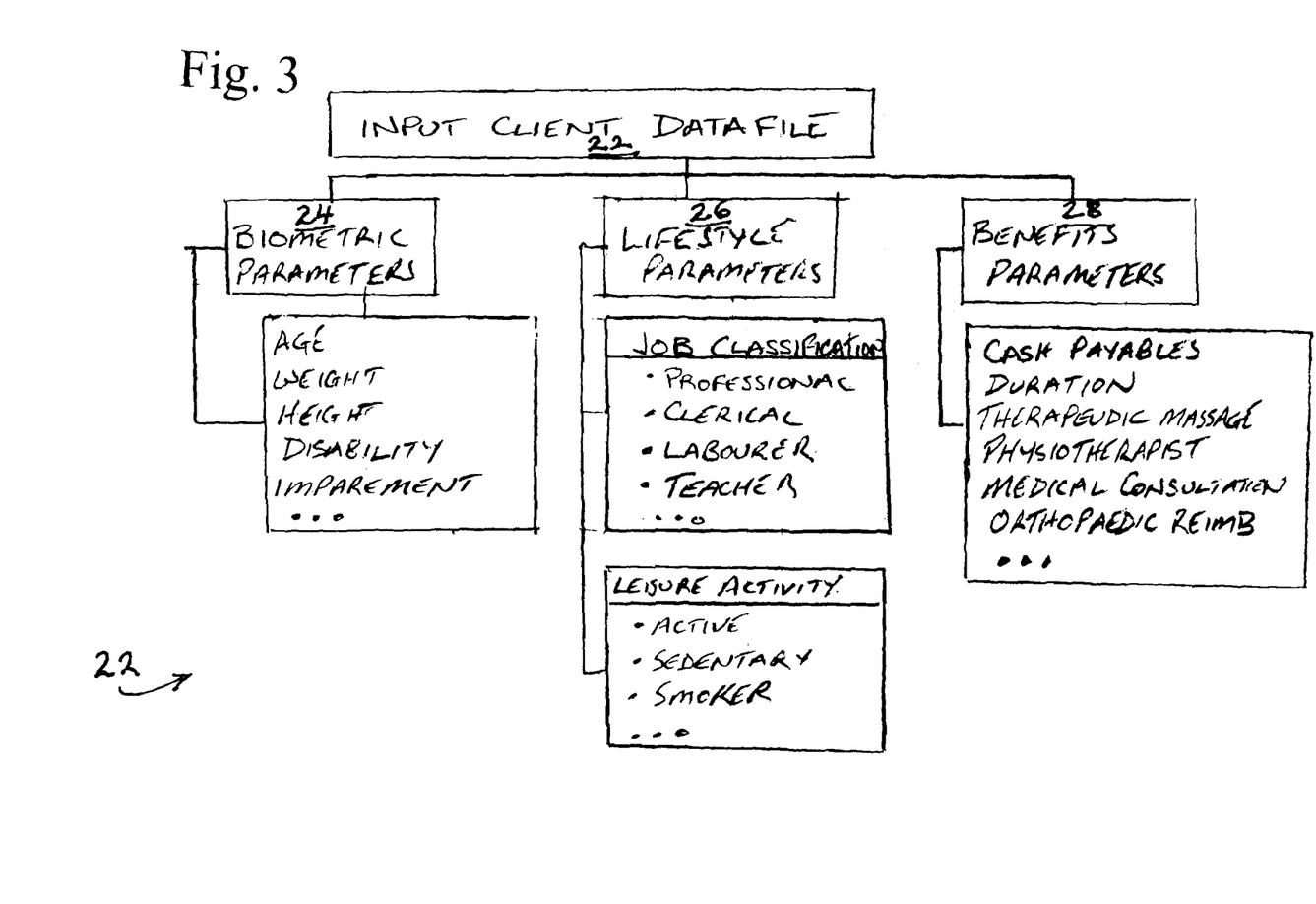
FIG. 3 illustrates schematically the input client datafiles used in the data management system used in the monitoring system of FIG. 1.

The input client datafile 22, shown best in FIG. 3, includes memory for storing input client data. The input client data contains information specific to the individual user 8. As shown best in FIG. 3, the client datafile 22 preferably includes user specific biometric parameters 24, user specific lifestyle parameters 26, as well as user specific benefit parameters 28. Biometric parameters 24 most preferably relate to the individual's physical status including the user's age, weight, height, as well as indications respecting any disability to be treated as part of the rehabilitative programme, or other impairments which for example, may result from pre-existing injuries. Disabilities to be treated may, by way of non-limiting example, include the partial paralysis of the user's legs or arms resulting from stroke or physical trauma, mobility loss resulting from spinal injuries, or muscular or skeletal damage caused by load straining or repetitive stress movements.

Lifestyle parameters 26 most preferably include particulars as to the user's profession, as well as indications of the user's leisure activities. Leisure activity particulars may include whether the individual is highly active and exercises regularly, smokes, any drug or prescription usage or whether the user has a sedentary lifestyle. Although not essential, most preferably, the lifestyle parameters are used to provide a weighting (i.e. active, inactive) of any pre-injury/trauma personal health or performance index (PI).

The individual benefit parameters 28 included in the input client datafile 22 may include without restriction, a dollar amount that the user 8 is entitled to receive in either disability or workers compensation payments under either an at-fault or no-fault insurance regime; particulars as to benefit duration where payments are time defined; as well as collateral non-monetary benefits, such as access credits for counselling, message therapy, hydrotherapy, prosthetic entitlement and the like.

Figure 4:
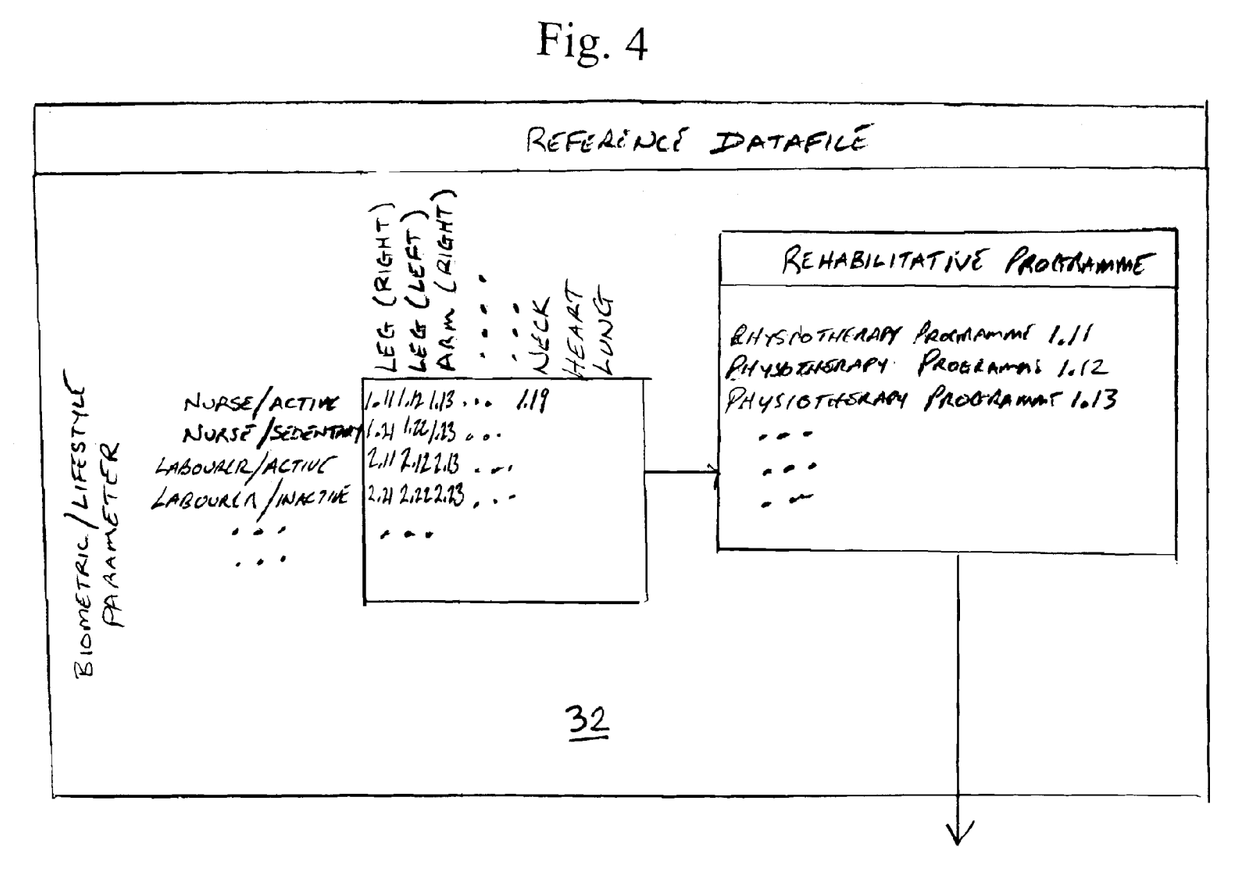
FIG. 4 illustrates schematically the reference datafile architecture used in the data management system used in the monitoring system of FIG. 1.

As shown best in FIG. 4, the reference datafile 32 includes a series of individual downloadable rehabilitative physiotherapy programmes. Each downloadable rehabilitative programme is chosen to correlate to a preselected exercise for a given injury type. The stored programmes furthermore stipulate preferred user specific target heart rates, and preferred caloric and energy or joule expenditure standards for the particular type of exercise, and are furthermore linked to the biometric and lifestyle parameters for the user 8 over a preselected period of time. Each of the physiotherapy programmes typically also include downloadable aural and/or video instructions as well as music, which provide to the user 8 with instructions to undertake physical activities ranging from stair climbing, to walking or lifting, or more intense cardiovascular workouts which are of a chosen duration and/or intensity. The physical activities are selected having regard to a particular time of day, and are chosen to achieve a predetermined heart rate and caloric and/or energy burn. It is envisioned that the physiotherapy programmes stored in the datafile 32 each provide preferred heart rate and caloric and joule expenditure standards to be achieved throughout individual time segments, such as each half-hour, hour or two-hour period of an average waking day. The expenditure standards account for the user 8 not only undertaking a robust rehabilitative therapeutic exercise for a selected time segment (i.e. a particular hour), but also in undertaking day-to-day activities for a given time As shown best in FIGS. 4 and 5, in one possible architecture, the physiotherapy programmes are individually correlated to specific biometric and lifestyle parameters. Preferably, each programme is furthermore correlated to a specific muscle, limb or malady in need of rehabilitation. In this regard, each general class of job category is pre-allocated with an average daily caloric/joule expenditure for selected time segments (i.e. each hour/pre-breakfast etc.) throughout the day, and which are in turn correlated to the specific user disability/impairment in need of rehabilitation.

Figure 5:
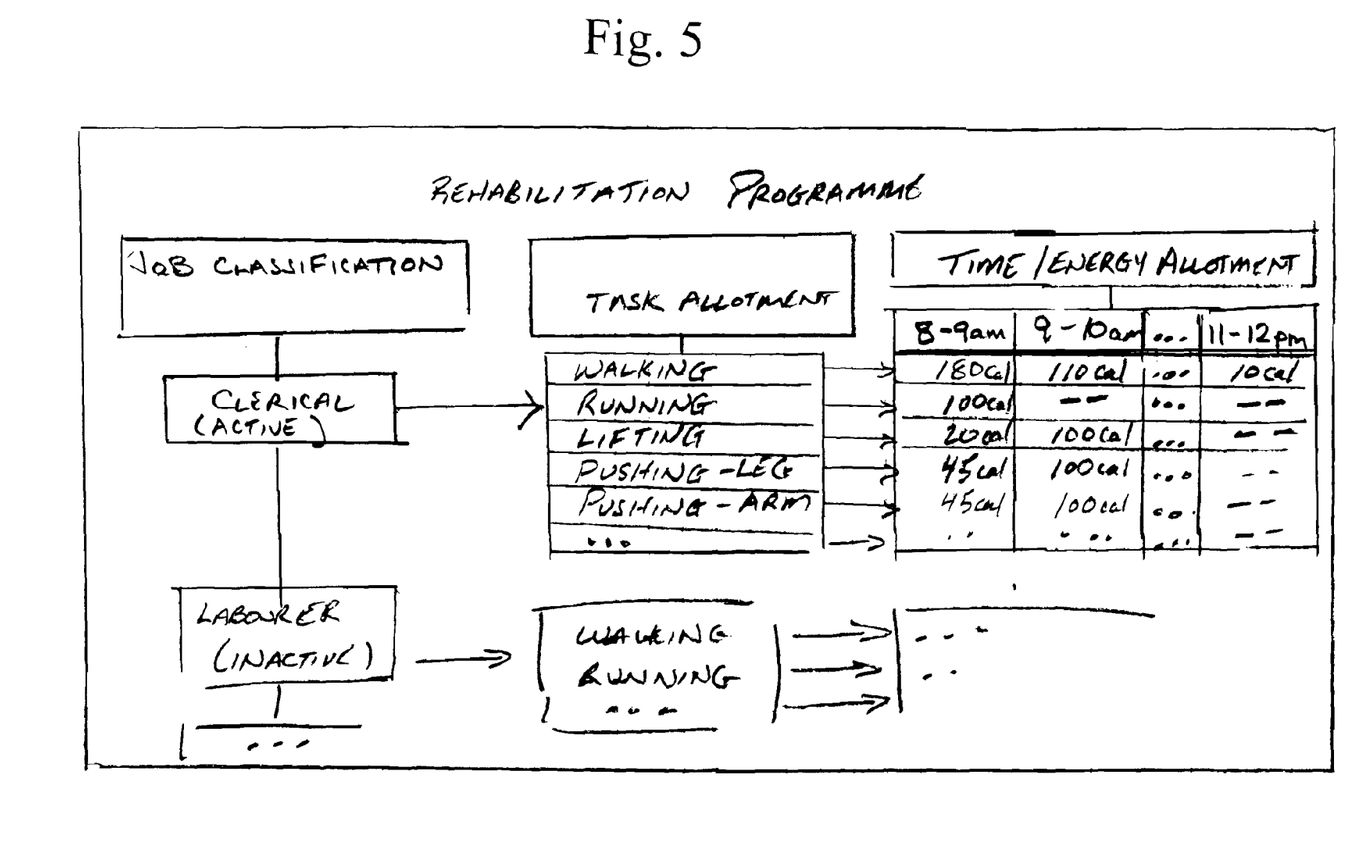
FIG. 5 illustrates schematically a preferred rehabilitation programme architecture used in the reference datafiles of FIG. 4.

The physiotherapy programme provided by the CPU 20 is most preferably calibrated to increase or decrease desired heart rate and/or physical activity target expenditures in accordance with projected expenditures having regard to healthy individuals with equivalent lifestyle parameters, the specific time of day and anticipated activity. For example, during weekday business hours, the downloaded physiotherapy programme adjusts to reflect that the user's ability to provide elevated heart rates and physical activities may be limited by his/her employment duties. During these time segments, the target data operates to provide only moderate visual cues to the user 8 to adjust heart rate or activities tailored to both desired rehabilitative exercises and real world expectations.

Figure 2:
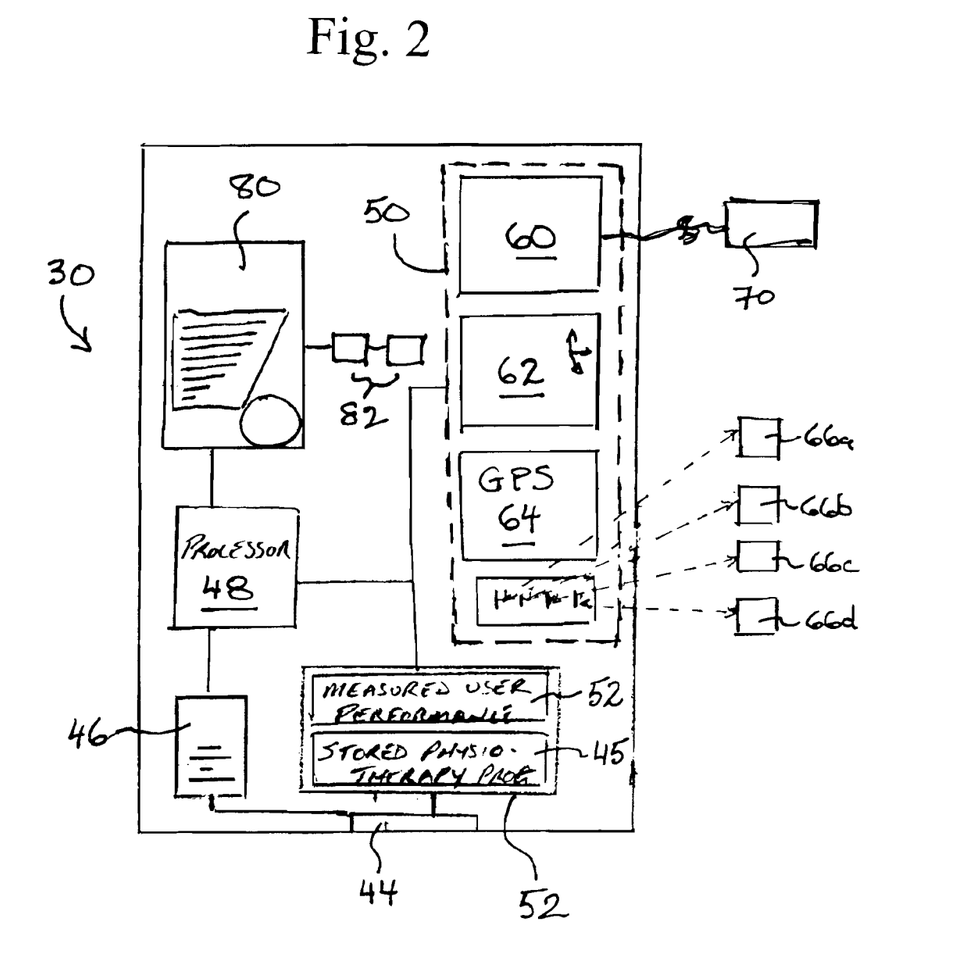
FIG. 2 illustrates schematically the wearable monitoring unit (WMU) used in the monitoring system of FIG. 1.

FIG. 2 shows schematically the wearable monitoring unit 30. The WMU 30 is operable to communicate with the central processing unit 20 to both download and store a user specific rehabilitative physiotherapy programme 45 thereto, as well as to upload the user's validated performance or compliance data. In a simplified mode of operation, data transfer between the CPU 20 and the WMU 30 is achieved by the uploading and downloading of datafiles via a PC (not shown) through a communicating network 35 such as a conventional home internet connection. Data downloading between the WMU 30 and the network 35 is achieved through a hardwired connection to the PC. FIG. 2 shows best each WMU 30 as having a internal USB connector port 44. The connection port 44 is used for electronically coupling the WMU 30 with the PC docking station (not shown) so as to facilitate the electronic downloading and uploading of programmes and data. Alternatively, the WMU 30 may also incorporate a wireless radio module operable to communicate to a base housed station, such as a wireless router on a PC network. Wireless module communications may be activated through a hall-effect sensor which is operable to detect a magnet housed in the docking station at a physiotherapist or home PC. Alternatively, the PC could be omitted entirely, with either wireless or direct wired communication occurring between the CPU 20 and WMU 30, or by hardwiring, or direct plug-in.

As indicated, each WMU 30 has an overall size and weight selected so as to be comfortably worn by the user 8 as a fully portable device. The WMU 30 is therefore preferably provided as a small multi-function mobile fitness monitoring and tracking device. The WMU 30 is adapted to be worn comfortable by the user 8 throughout the entire waking day, as he or she performs not only a specific physiotherapy or rehabilitative workout, but also most daily tasks. The WMU 30 is operated by way of a rechargeable battery 46 and preferably is approximately the size of a small cell phone or pager. The rechargeable battery 46 is chargeable through the USB connection port 44 in a conventional manner, as for example during data downloading and uploading from the PC, or a wall charging device. A sleep mode and wake-up function are preferably used to conserve power and provide an expected battery life in excess of seven days.

In addition to the battery 44, the WMU 30 is provided internally with an internal calendar/clock processor 48, a performance sensor array 50 and internal portable data storage/memory 52. The sensor array 50 includes a number of different types of sensors used to measure different physical attributes of the user 8 over the course of the preselected time segments, such as each hour, throughout the waking day. As will be described, the sensor array 50 is electronically linked to both the clock/processor 48 and the data storage/memory 52 to allow for the comparison and validation of measured user data, such as heart rate, caloric burn and/or energy burn, against the preselected target values provided by the selected physiotherapy programme 45 download from the CPU 20.

Preferably the sensor array 50 includes a heart rate sensor 60, an internal unit accelerometer 62, a global positioning sensor (GPS 64), and where the WMU 30 is used in the validation of a physiotherapy programme 45 for providing rehabilitative therapy for one or more of the user's 8 limbs, a number of force micro-sensors 66a, 66b, 66c, 66d. The heart rate sensor 60 includes a remote contact sensor pad 70 which is adapted for placement against a pulse point on the user's 8 skin in the monitoring and recording of heart rate data signals which reflect the user's heart rate during WMU 30 operation. Most preferably the WMU 30 incorporates as sensor 60, a means of wirelessly receiving heart rate pulse data from a wireless chest strap heart rate sensor device. Heart rate data is monitored and stored periodically (i.e. every 5 minutes) in the memory 52. More preferably heart rate variability is also calculated and stored as a value. As will be described, the heart rate sensor 60 is used to monitor whether or not a prescribed target heart rate has been achieved for a given time segment through the entire day. This measured heart rate is then compared against the target heart rate for the corresponding time segment in the preselected physiotherapy programme 45.

The internal accelerometer 64 is preferably of a 3-axis operational design which is used to measure whole body motion when the WMU 30 is worn on the user 8. By providing a belt mount 47, the orientation of the accelerometer 62 with relation to the user's 8 body is advantageously fixed so that the output from each axis is directionally known. In one preferred operational mode, the x-axis is down (giving a +1 g signal when stationary). The y-axis is selected forward and the z-axis is inwardly towards the body (i.e. twisting). In general, the accelerometer 62 signals are continuously analysed together with signals from the GPS sensor 64 and the type of activity determined, with both the activity type and activity dynamic energy stored in memory 52. The data can then be analyzed in real time, and in this manner, the types and extent of activity detected are:
    Walking and distance; (Note: Position the device)
    Running and distance; (as a body motion and analysis)
    Jumping and distance; (device that can be used to determine steps as one of its functions)
    Sitting/Standing
    Lying Down
    Rolling Passive transportation distance (i.e. car or other transportation journey).

Dynamic energy and activity

The accelerometer 62 is thus operable to monitor and output joule data signals which provide an indication of the movement of the user 8. Additionally, the microprocessor 48 provides an analysis algorithm used to filter the accelerometer 62 data and determine the validity of a step. Step count and time is then recorded and saved as time-stamped measured user performance data in the memory 52 periodically (i.e. every 5 minutes). In addition the bounce height of the x-axis will be analysed to gain a measure of distance travelled during each step.

The force micro-sensors 66a, 66b, 66c, 66d are provided in a preferred embodiment in the form of miniature remote accelerometer sensors such as micro-miniature piezoelectric accelerometers. In the case of leg or arm injuries, the sensors 66 adapted for direct securement to the limbs of the user 8 in the manner shown in FIG. 6. The micro-sensors 66 preferably provide joule data signals to the processor 48 which are indicative of the movement of the specific limb in need of physiotherapy, and/or the physical force or exertion preformed thereon throughout the day. Sensors 66 are most preferably wirelessly linked to the WMU 30, although hardwired sensors may also be used.

The clock/micro-processor 48 allows the data collected by the heart rate sensor 60, accelerometer 62, GPS 64 and force micro-sensors 66 to be time-stamped. The microprocessor 48 preferably also controls all WMU 30 operational features, and includes self-testing and diagnostics functions. This information is uploadable to the CPU 20 so that functional errors with the WMU 30 can be indicated to the user 8. The microprocessor 48 manages the WMU 30 data storage/memory 52.

In a simplified construction a master output display 80 and operational mode control buttons 82, allow the user to select a specific operating mode for the WMU 30, and either upload to the CPU 20 data relating to the validation of the user's heart rate, caloric and/or energy expenditures and/or download physiotherapy programmes for playback. The device memory 52 is used to receive and store the preselected physiotherapy programme 45 which is downloaded by the CPU 20 and which is tailored specifically having regard to the input client data, having regard to the specific user injury or malady which is in need of rehabilitation. Optionally, the WMU 30 may operate a number of operational modes including: as an interactive device for a specified limited timed physiotherapy regime; as a daily monitor used to record the user's activity heart rate and caloric expenditure; and as a rehabilitation coach as part of an outpatient whole-day physiotherapy regime.

In the embodiment shown in FIG. 2, the WMU display 80 consists of an LED array which is divided into multiple sections. Although not essential, each section is preferably operable to provide feedback to the user 8 through a colour indication display. In a simplified design, the sections of the display 80 incorporate LEDs which are operable to emit the colours red, yellow or green as visual prompts to the user 8, to provide a visual indication of whether or not the user's 8 heart rate, caloric and/or joule expenditure and overall physical activity or total energy (joule) expenditure meets or exceeds the preselected target standards for the preselected physiotherapy programme 45 at each particular time segment or time of day. The display 80 provides a visual colour indicator of the comparison of the measured state of the user's heart rate, caloric and energy consumption, activity rate, and health as against pre-defined programme goals for both the particular day, and particular time segment as determined by the clock/microprocessor 48. The colour indicator feedback is activated by the output switch 82, with the goal for the user to achieve green for each section.

The internal processor 48 is operable to compare both the heart data signals, as well as the caloric and joule expenditure data signals which are received from the accelerometer sensor 62, GPS 64 and the force micro-sensors 66. The processor 48 then compares the measured user heart rate and joule data with the heart rate and joule expenditure standards which are contained the preselected physiotherapy programme 45 stored in the memory 52 and provide validated compliance output data 88. Although not essential, most preferably the comparison between the measured data and the stored standards is performed on a real-time basis by the processor 48 throughout the entire day, as the user 8 wears the device. Concurrently, the display 80 provides the user 8 with a visual indication of his/her compliance with the heart rate and expenditure standards. This advantageously allows the user 8 to implement minor, or of necessary major adjustment to his/her physical activities either in real-time or following each time segment, to ensure continued compliance with the preselected rehabilitation programme 45. In one possible mode, WMU 30 may produce a data table used to control the feedback light. This data is uploadable from the WMU 30 to the CPU 20 during the time it is connected to a PC. For the user 8, the data table is based on their information in a unique user account at the portal. Data may, for example, include the following Table 1.

TABLE 1

Date and Time
Degree of Movement
Movement Type
Heart Rate
HRV
Dynamic Energy
Activity Type The total PI expected could be calculated using Basal Metabolic Rate and Activity level (or similar), with or without other values based on the specific physiotherapy goals of the user 8 depending on his or her specific disability and/or malady. This value is then allocated to a specific pre-selected daily periods, as for example, is shown in Table 2.

TABLE 2

| Time Segment | Time | General PI to be Achieved | Physiotherapy Targets | Special or Additional Activity Targets |
|---|---|---|---|---|
| 1 | 12 am–6 am | 200 | 100 | 0 |
| 2 | 6 am–8 am | 400 | 0 | 0 |
| 3 | 1 pm–3 pm | 300 | 100 | 200 |
| 4 | 5 pm–9 am | 600 | 0 | 0 |

The present system preferably also allows the user 8 at the end of each segment to "top up" by performing additional therapeutic exercises so as to reach the total target caloric and/or joule burn and/or heart rate levels for a particular day. With the indication that the target heart and/or overall caloric and/or energy expenditure levels for a time segment has not yet been achieved, the user 8 may download from the CPU 30 a supplemental physiotherapy routine consisting of music, video and/or instructions. This downloaded routine is selected to enable the user 8 to complete the required level of necessary physiotherapy workout used to achieve the target fitness level and target heart level, and having regard to the actual measured values for the particular day. Following at the end of each day, the user may then upload from the WMU 30 data representative of actual physiotherapy activities and heart rate data.

In a preferred mode, the user's physical activity is measured throughout the day and tracked by the WMU 30 using the sensor array 50. The collected data is converted to the universal Performance Index (PI) scale based on the user's 8 pre-input physical characteristics. Feedback is customized to activity and energy expenditures throughout a day based on the user's 8 type of injury or malady and correlated physiotherapy programme which has been pre-selected. The portability and light weight of the WMU 30 allows it to be worn by the user 8 throughout his/her waking day to collect data relating to the user's overall heart rate, and energy and/or caloric expenditure. The data collected is uploaded (via PC) to the CPU 20 as a compliance output data 88 to provide feedback to the user's employer and/or physiotherapist. The uploaded compliance output data 88 provides an indication of whether the user's 8 caloric and/or joules expended as a result of the user's physical activity equals or exceeds the target level.

Although not essential, most preferably the compliance output value 88 is used to reset the categories and/or frequency or available user benefits stored within a benefits databank 90. The benefits databank 90 is then immediately or periodically downloaded from the central processing unit 20 to the benefit administrator datafile 40. The compliance output data 88 thus not only provides the employer or benefits administrator with an indication as to whether or not the user 8 is meeting target heart rate, caloric and/joule data expenditures in compliance with the selected physiotherapy programme, but also may be used to automatically adjust use, benefits and incentives. To provide an added incentive to the user 8 to maintain compliance with the physiotherapy programme, depending on the compliance output data 88, the benefits administrator datafile 40 may be adjusted to alter the user's benefits. In one scenario where the user 8 complies with the physiotherapy programme 45, the benefits databank 90 is operated to increase benefit payments over the early part of the rehabilitation schedule. This may advantageously provide positive reinforcement resulting in the user's earlier recovery, and an earlier return to work. Conversely, a user 8 could be penalized, receiving reduced benefits if the compliance output data 88 indicates the user 8 is not maintaining an acceptable level of conformity to the rehabilitative physiotherapy programme 45. Such reduced benefits could include, by way of non-limiting example, either a restriction in non-monetary benefits, or a reduction in the value and/or frequency of momentary benefits paid to the user 8.

Although the detailed description describes the system 10 as being used in the monitoring of the user's 8 compliance with a rehabilitative physiotherapy regime, the invention is not so limited. In an alternate application, the system could be used as a general ergonomic monitoring system by employers. It is envisioned that the present system 10 may advantageously be used to allow the monitoring of employee compliance with one or more preselected wellness and/or lifestyle programmes. Such wellness programmes may be selected, again having regard to essentially the same biometric and lifestyle parameters of the employee.

It is to be appreciated that employee wellness and ergonomic programmes are selected to provide an overall health benefit to the employee, with a view to reducing employee absenteeism and increasing overall health. In such an application, the employer may also provide incentives for employee participants, such as increased pay, time off or access to health facilities or other non-monetary benefits. The system 10 of such an application would operate in substantially the same manner as that previously described with a view to providing reduced health benefit costs to the employer.

Although the preferred embodiment describes the WMU 30 as having a clock/processor 48 and memory 52 operably to store and validate measured user performance data 52 with the downloaded standards, the invention is not so limited. In a more economical construction, data storage and validation processing may be achieved by way of a user's home personal computer or PC. A user's PC may also be provided to facilitate date and firmware downloads between the CPU 20 and WMU 30. User performance information from the WMU 30 may also be stored directly on a PC, allowing the user to monitor any changes in performance data and obtain feedback therefrom. In a more preferred construction, a firmware version is saved which is unique to the device ID for the WMU 30 at the CPU 20. Any firmware updates will be posted on the CPU 20 and downloaded as appropriate.

Optionally, the physiotherapy database may be connected to the central CPU 20 to automatically upload information with respect to the user's in hospital physiotherapy regime.

Although not essential, in a preferred construction a digital audio video player 80 is preferably also provided within the WMU 30 which allows music, video and/or audio instructions to be downloaded from the CPU 20 for playback to the user 8.

Although the detailed descriptions and illustrates various preferred embodiments, the invention is not so limited. Many modifications and variations will occur to persons skilled in the art. For a definition of the invention, reference may now be had to the appended claims.

I claim:

1. An apparatus for ensuring a user's compliance with a preselected physiotherapy program over a selected time period, the apparatus comprising:
    a wearable monitoring device being operable to measure at least one of said user's caloric and joule expenditure over the selected time period, the monitoring device having:
        an internal clock,
        memory for storing said preselected physiotherapy program as downloaded user specific heart rate and joule expenditure standards over the selected time period,
        a heart rate monitoring sensor for monitoring and outputting heart rate data signals indicative of said user's heart rate over the selected time,
        at least one accelerometer for monitoring and outputting joule data signals indicative of at least one of movement by said user and physical force on at least part of said user's body over the selected time period,
        a plurality of force micro-sensors which are attachable to at least part of said user's body in need of rehabilitation, and
        an internal processor for comparing said heart rate data signals and said joule data signals to said user specific heart rate and joule expenditure standards over said selected time period, and outputting a compliance output value which is dependent on the comparison, said force micro-sensors operable to provide data signals to said internal processor representative of energy expenditure by said at least part of said user's body; and a computerized device for communicating with the wearable monitoring device, the computerized device having:

a reference database for storing datafiles providing preferred target heart rate and joule expenditure standards for a plurality of rehabilitation programs, said rehabilitation programs correlated to a biometric parameter, a lifestyle profile parameter and an injury or malady type to be rehabilitated, said biometric parameters comprising at least one of said user's age and weight, a client database for storing input client data indicative of each of said user's injury or malady, said user's biometric parameters, lifestyle profile information for said user, and benefit data correlated to a user's health benefit, and a processing unit operable to output as said preselected physiotherapy program a selected one of said rehabilitation programs correlated to said input client data;

wherein said compliance output value is dependent upon inputting said client data into said client database, downloading said preselected physiotherapy program to said wearable device, and with said user wearing said wearable device during said selected time period, actuating said internal processor to compare said heart rate signals and said joule data signals to said user specific heart rate and joule expenditure standards to generate said compliance output value, said outputted compliance value displayed on said wearable device to serve as a user specific indicator of compliance, and wherein said rehabilitation program is correlated to an injury to the at least part of said user's body;

and wherein the user's health benefit is adjusted based on the compliance output value.

2. The apparatus of claim 1, wherein the wearable monitoring device includes a display for providing a visual representation of said compliance output value and any modification or potential modification to the user's health benefit data to the user.

3. The apparatus of claim 2, wherein said biometric parameters comprise each of said user's age and weight, and said lifestyle profile information comprises at least one of a categorization of said user's job, weighting factors respecting the user's pre-injury health and indication of any pre-existing user disabilities.

4. The apparatus of claim 2, wherein said lifestyle profile parameters include data selected from preselected classes of job categories, and preselected classes of leisure activity categories.

5. The apparatus of claim 2, wherein said wearable monitoring device is a portable monitoring device operable to provide said visual representation of said output value data substantially in real time.

6. The apparatus as claimed in claim 2, wherein the selected time period comprises at least eight hours.

7. The apparatus as claimed in claim 2, wherein the selected time period comprises an average waking times over at least a one week interval.

8. The apparatus as claimed in claim 1, wherein said wearable monitoring device is operated to provide a visual indication to said user in response to the compliance output value which is indicative of any modification to the user's health benefit data.

9. An apparatus for monitoring and validating compliance with a preselected wellness or physiotherapy program by a user, the apparatus comprising:

a wearable monitoring device being operable to measure said user's total daily caloric expenditure, the monitoring device having, an internal clock, memory for storing said selected wellness and rehabilitation physiotherapy program as time dependent user specific heart rate and caloric and/or joule expenditure standards for a preselected time period, a heart rate monitoring sensor for monitoring and outputting heart rate data signals indicative of said user's heart rate, and an accelerometer for monitoring and outputting at least one of caloric and joule data signals indicative of at least one of movement by said user and physical force on at least part of said user's body, at least one force micro-processor which is attachable to at least part of said user's body, a processor for receiving said heart rate data signals and said caloric and/or joule data signals as input values and validating said input values to said user specific heart rate and at least one of caloric and joule expenditure standards over said preselected time period, and using a comparator outputting a compliance output data indicative of any difference between said input values and said user specific heart rate and at least one of caloric and joule expenditure standards, wherein the at least one force micro-processor is operable to provide data signals to said processor representative of said user's energy expended by movement of said at least part of said user's body;

a computerized device for communicating with the wearable monitoring device, the computerized device having:

a reference database for storing a plurality of datafiles providing preferred target heart rate and at least one of caloric and joule expenditure standards for a plurality of wellness and rehabilitation programs correlated to an injury, disability and a lifestyle profile, and a preselected biometric parameter, said biometric parameters comprising at least one of user age, and weight, a client database for storing client data indicative of biometric parameters of said user and at least one of a disability, injury and lifestyle profile of said user, and storing benefit data correlated to a user's health benefit, and a processing unit operable to output as said preselected wellness or physiotherapy program a selected one of said wellness and rehabilitation programs which correlates at least in part to at least one of said user's injury, disability and lifestyle profile, and said preselected biometric parameters, wherein said selected wellness and physiotherapy program comprises a rehabilitative physiotherapy program for providing a therapeutic benefit in remediation to an injury to said at least part of said user's body, and wherein the user's health benefit is adjusted based on the compliance output data; and a non-compliance alert unit including a display for providing said user with a visual representation of non-compliance based on said difference.

10. The apparatus of claim 9, wherein said lifestyle profile includes data selected from preselected job categories, and preselected leisure activity categories.

11. The apparatus of claim 9, wherein said wearable monitoring device is a portable monitoring device operable to provide said visual representation of said output value data substantially in real time.

12. The apparatus of claim 9, wherein the preselected time period comprises an average waking day.

13. The apparatus of claim 9, wherein said selected wellness and physiotherapy program comprises a rehabilitative therapy program, said at least one of caloric and joule expenditure standards comprising joule expenditure standards for a selected injured body part, and wherein said at least part of said user's body is a part in need of rehabilitative physiotherapy.

14. The apparatus of claim 13, wherein said client data further includes benefit data correlated to a health or monetary benefit to said user, the computerized device operable to receive the compliance output data and modify the benefit data for the user in response to compliance output data.

15. The apparatus as claimed in claim 14, comprising, inputting said client data into said client database, downloading said selected program to said wearable device in response to said input data, and with said user wearing said wearable device during said selected time period, actuating said internal processor to compare said user heart rate signals and said joule data signals to said user specific heart rate and joule expenditure standard to output said compliance output data, and modifying the user's health benefit data in response to the compliance output data.

16. The apparatus as claimed in claim 14, wherein said wearable monitoring device is operated to provide a visual indication to said user in response to an actual or potential change to the user's benefit data.

17. A method of using a wearable monitoring device for validating a user's compliance with a physiotherapy program selected to provide a therapeutic advantage to the user, the wearable monitoring device including a heart rate monitoring sensor for monitoring and outputting heart rate data signals indicative of said user's heart rate, and an accelerometer for monitoring and outputting at least one of caloric and joule data signals indicative of at least one of movement by said user and physical force on at least part of said user's body, the method comprising, attaching at least one force micro-sensor to at least part of said user's body in need of wellness or physiotherapeutic exercise, wherein the at least one force micro-sensor includes processor circuitry for receiving force signals from said micro-sensor which are representative of measured forces applied to said part of said user's body, storing a plurality of datafiles for preferred target heart rate and caloric and joule expenditure standards for a plurality of rehabilitation programs in a reference database, said rehabilitation programs correlated to preselected biometric parameters and injury type, said biometric parameters comprising at least said user's age and weight, storing input client data indicative of a user's injury, age, weight, and benefit data correlated to a user's health benefit within a client database, downloading to the wearable monitoring device as said physiotherapy program a selected rehabilitation program correlated to the user's input client data using at least one communicating network, using a processing unit, validating as input values said heart rate data signals and said at least one of caloric and joule data signals to said user specific heart rate and at least one of caloric and joule expenditure over a preselected time period, and outputting using a comparator a compliance output data indicative of any difference between said input values and said user specific heart rate and said at least one of caloric and joule expenditure, and validating said force signals as part of said input values, displaying an alert relating to non-compliance as indicated by any difference between said input values and said user specific heart rate and said at least one of caloric and jewel expenditure;

recording a change in said benefit data in response to the compliance output data; and adjusting the user's health benefit based on the compliance output data.

18. The method of claim 17 further comprising displaying to said user a visual representation of said compliance output data which is indicative of any change or potential change in said benefit data.

19. The method of claim 18, wherein the visual representation is displayed to said user substantially in at least a bi-hourly frequency substantially throughout the user's waking day.

20. The apparatus of claim 1, wherein said rehabilitation program is correlated to an injury to at least one of said user's arm and leg, wherein said plurality of force micro-sensors are attachable to an arm and leg in need of rehabilitation, said force micro-sensors operable to provide data signals to said internal processor representative of energy expenditure by said at least one of arm and leg.

21. The apparatus as claimed in claim 9, wherein said rehabilitative physiotherapy programs provides a therapeutic benefit in remediation to an injury to said user's limbs, wherein said force micro-processor is attachable to an injured limb for providing data signals to said processor representative of said user's energy expended by movement of said injured limb.

22. The method of claim 17, wherein said at least one force micro-sensor is attachable to a limb of said user, and said processor circuitry receives force signals from said micro-sensor which are representative of measured movements and forces applied to said limb.

* * * * *